(12) United States Patent
Potyrailo et al.

(10) Patent No.: US 7,807,473 B2
(45) Date of Patent: Oct. 5, 2010

(54) MATERIAL COMPOSITIONS FOR SENSORS FOR DETERMINATION OF CHEMICAL SPECIES AT TRACE CONCENTRATIONS AND METHOD OF USING SENSORS

(75) Inventors: Radislav A. Potyrailo, Niskayuna, NY (US); Timothy M. Sivavec, Clifton Park, NY (US); Caibin Xiao, Harleysville, PA (US); Theodore J. Cecconie, Buckingham, PA (US); Lamyaa Hassib, Niskayuna, NY (US); Andrew M. Leach, Clifton Park, NY (US); David B. Engel, The Woodlands, TX (US)

(73) Assignee: General Electric Company, Schenectady, NY (US)

( * ) Notice: Subject to any disclaimer, the term of this patent is extended or adjusted under 35 U.S.C. 154(b) by 1066 days.

(21) Appl. No.: 11/259,506

(22) Filed: Oct. 26, 2005

(65) Prior Publication Data

US 2007/0092973 A1    Apr. 26, 2007

(51) Int. Cl.
*G01N 21/00* (2006.01)
(52) U.S. Cl. .............. 436/164; 436/166; 436/167; 436/169; 436/171; 436/172; 436/800; 436/805; 422/50
(58) Field of Classification Search .............. 436/163, 436/164, 800, 805; 422/85
See application file for complete search history.

(56) References Cited

U.S. PATENT DOCUMENTS

| | | | | |
|---|---|---|---|---|
| 3,998,878 A | * | 12/1976 | Hearon et al. | 562/577 |
| 4,503,156 A | * | 3/1985 | Yamazato et al. | 436/79 |
| 5,005,572 A | | 4/1991 | Raemer et al. | |
| 5,116,759 A | * | 5/1992 | Klainer et al. | 435/287.2 |
| 5,482,866 A | * | 1/1996 | Denton et al. | 436/79 |
| 5,744,794 A | * | 4/1998 | Michie et al. | 250/227.16 |
| 5,790,627 A | * | 8/1998 | Iketaki | 378/43 |
| 6,011,882 A | * | 1/2000 | Dasgupta et al. | 385/12 |

(Continued)

FOREIGN PATENT DOCUMENTS

EP    0 952 451    10/1999

(Continued)

OTHER PUBLICATIONS

Miniaturized Biosensors Employing Electropolymerized Permselective Films and Their Use for Creatinine Assays in Human Serum, Marcel B. Madaras and Richard P. Buck, Anal. Chem. 1996, 68, 3832-3839.*

(Continued)

*Primary Examiner*—Jill Warden
*Assistant Examiner*—Dean Kwak
(74) *Attorney, Agent, or Firm*—Wegman, Hessler & Vanderburg

(57) ABSTRACT

A method of quantitatively measuring the concentration of a chemical species in a sample solution with a sensor film. A hydrogel sensor film is prepared having a chemical composition comprising an indicator that changes its optical property in the ultra-violet, visible or near-infrared spectral range upon being exposed to the chemical species in the sample solution. The film is exposed to a fixed amount of the sample solution. The concentration of the chemical species in the sample solution is quantified using the average absorbance measured from the sensor film.

17 Claims, 15 Drawing Sheets

Typical set of spectra of a molybdate sensor film device at various molybdate concentrations.

U.S. PATENT DOCUMENTS

| | | | |
|---|---|---|---|
| 6,046,052 A * | 4/2000 | Arter et al. | 436/86 |
| 6,627,177 B2 * | 9/2003 | Singaram et al. | 424/9.6 |
| 2003/0022094 A1 * | 1/2003 | Nakamura et al. | 430/157 |
| 2003/0035917 A1 * | 2/2003 | Hyman | 428/67 |
| 2003/0217808 A1 * | 11/2003 | Woods et al. | 156/332 |
| 2005/0113546 A1 * | 5/2005 | Tao et al. | 528/29 |
| 2006/0009805 A1 * | 1/2006 | Jensen et al. | 607/2 |
| 2006/0234384 A1 * | 10/2006 | Kaufman | 436/79 |

FOREIGN PATENT DOCUMENTS

| | | |
|---|---|---|
| WO | WO 99/09406 | 2/1999 |
| WO | WO 00/02845 | 1/2000 |
| WO | WO 2005/066275 | 7/2005 |

OTHER PUBLICATIONS

Polymers in sensor applications, Basudam Adhikari, Sarmishtha Majumdar, Prog. Polym. Sci. 29 (2004) 699-766.*

Koichi Yamamoto; Interaction Between Sulphonephthalein Dyes and Quaternary Ammonium Ions in Aqueous Solution, Analytical Sciences, Jun. 1992, vol. 8, Japan.

Koronczi et al.; Submicron Sensors for Ion Detection Based on Measurement of Luminescence Decay Time; Sensors and Actuators B 74 (2001) 47-53, Germany.

Kosch et al.; Strategies to Design pH Optodes With Luminescence Decay Times in the Microsecond Time Regime, 1998, 70, 3892-3897; Insitute of Analytical Chemistry, Germany.

Munoz, M.A. et al., "Direct Determination of Inorganic Phosphorus in Serum with a Single Reagent", Clinical Chemistry, vol. 29, No. 2, (1983) pp. 372-374.

* cited by examiner

Figure 1: Typical set of spectra of a molybdate sensor film device at various molybdate concentrations.

Figure 2: Typical response curve of a molybdate sensor film device to various molybdate concentrations.

Figure 3: Typical set of spectra of a magnesium sensor film device at various magnesium concentrations.

Figure 4: Typical response curve of a magnesium sensor film device to various magnesium concentrations.

Figure 5: Typical set of spectra of a hardness sensor film device at various hardness concentrations.

Figure 6: Typical response curve of a hardness sensor film device to various hardness concentrations.

Figure 7: Typical set of spectra of a calcium sensor film device at various calcium concentrations.

Figure 8: Typical response curve of a calcium sensor film device to various calcium and magnesium concentrations.

Figure 9: Typical set of spectra of a sulfite sensor film device at various sulfite concentrations in a typical boiler water matrix, at pH 10

Figure 10: Typical response curve of a sulfite sensor film device to various sulfite concentrations in a typical boiler water matrix, at pH 10.

Figure 11. Typical set of spectra of a sulfite sensor film (prepared to withstand highly alkaline, high pH water samples) at various sulfite concentrations in a typical boiler water matrix, at pH 12, 1000 mg/L M-alkalinity.

Figure 12. Typical response curve of sulfite sensor film (prepared to withstand highly alkaline, high pH water samples) to various concentrations in a typical boiler water matrix, at pH 12, 1000 mg/L M-alkalinity.

Figure 13. Alkalinity calibration curve

US 7,807,473 B2

MATERIAL COMPOSITIONS FOR SENSORS FOR DETERMINATION OF CHEMICAL SPECIES AT TRACE CONCENTRATIONS AND METHOD OF USING SENSORS

BACKGROUND OF THE INVENTION

1. Field of the Invention

The present invention relates generally to sensors used in optical analysis of samples, and in particular relates to the material composition of sensors and methods for measuring trace concentrations of chemical species using the sensors.

2. Description of Related Art

Sensor methods and sensor films for quantification of volatile and nonvolatile compounds in fluids are known in the art. Typically, quantification of these parameters is performed using dedicated sensor systems that are specifically designed for this purpose. These sensor systems operate using a variety of principles including electrochemical, optical, acoustic, and magnetic. For example, sensor systems are used to conduct optical inspection of biological, chemical, and biochemical samples. A variety of spectroscopic sensors operating with calorimetric liquid and solid reagents have been developed. In fact, spectophotometric indicators in analytical chemistry have become the reagents of choice in many commercially available optical sensors and probes.

Optical sensors possess a number of advantages over other sensor types, the most important being their wide range of transduction principles: optical sensors can respond to analytes for which other sensors are not available. Also, with optical sensors it is possible to perform not only "direct" analyte detection, in which the spectroscopic features of the analyte are measured, but also "indirect" analyte determination, in which a sensing reagent is employed. Upon interaction with the analyte species, such a reagent undergoes a change in its optical property, e.g. elastic or inelastic scattering, absorption, luminescence intensity, luminescence lifetime or polarization state. Significantly, this sort of indirect detection combines chemical selectivity with that offered by the spectroscopic measurement and can often overcome otherwise troublesome interference effects.

Because spectophotometric indicators were originally developed for aqueous applications, their immobilization into a solid support is a key issue for their application in optical sensing. Polymeric materials for reagent-based optical sensors are often complex multicomponent formulations. The key formulation ingredients include a chemically-sensitive reagent (indicator), a polymer matrix, auxiliary minor additives, and a common solvent or solvent mixture. However, it is difficult to predict the best formulation of the sensor material to yield a certain desired functionality.

Thus, there exists a strong need for simplified sensors that can easily be used to carry out optical analysis of multiple quantitative assays and/or other biological, chemical, and physical environmental parameters with high reproducibility that yield improved sensor sensitivity, decreased response to interferences, enhanced stability, and other desired parameters.

SUMMARY OF THE INVENTION

In one aspect, the invention is directed to a method of quantitatively measuring the concentration of a chemical species in a sample solution with a sensor film. The method includes preparing a hydrogel sensor film having a chemical composition comprising an indicator that changes its optical property in the ultra-violet, visible, near-infrared spectral range upon being exposed to the chemical species in the sample solution. The method further includes exposing the film to a fixed amount of the sample solution. The method further includes measuring the absorbance of the film at a wavelength near the maximum absorbance peak ($\lambda$max) of the indicator using optical scanning equipment. The method also includes quantifying the concentration of the chemical species in the sample solution using the average absorbance measured from the sensor film.

Another aspect of the invention is a method of quantitatively measuring the concentration of a chemical species in a sample solution with a plurality of sensor films. The method includes preparing a plurality of hydrogel sensor films that change their optical property in the ultra-violet, visible, or near-infrared spectral range upon being exposed to the chemical species in the sample solution, wherein the chemical composition added in the hydrogel films comprises a pH indicator, a surfactant, and an acid. The method also includes varying the acid concentration in each of the plurality of films by a predetermined pattern. The method also includes exposing the films to a fixed amount of the sample solution. The method further includes measuring the absorbance of the films at a wavelength near the maximum absorbance peak ($\lambda$max) of the indicator using optical scanning equipment and quantifying the concentration of the chemical species in the sample solution using the average absorbance measured from the sensor films.

In another aspect, the invention is directed to sensor used in determining the concentration of chemical species in a sample at trace concentrations. The sensor includes a hydrogel sensor film comprising a quaternary ammonium salt, quaternary phosphonium salt or a quaternary imidazolium salt, and an indicator. The indicator changes its optical property in the ultra-violet, visible, or near-infrared spectral range upon being exposed to the chemical species in the sample solution. The indicator is immobilized in the hydrogel film by forming an ion pair with the quaternary ammonium ion, wherein the concentration of quaternary ammonium salt is substantially higher that the stoichiometric amount required to ion pair.

In another aspect, the invention is directed to sensor used in determining the concentration of chemical species in a sample at trace concentrations. The sensor includes a hydrogel sensor film comprising an indicator and an additive that increases the sensor sensitivity of response to chemical species where the additive is a polymer and where the sensor film is prepared by dissolving hydrogel, indicator, and second polymer in a common solvent mixture. The indicator changes its optical property in the UV, ultra violet, visible near-infrared spectral range upon being exposed to the chemical species in the sample solution.

The present invention and its advantages over the prior art will become apparent upon reading the following detailed description and the appended claims with reference to the accompanying drawings.

BRIEF DESCRIPTION OF THE DRAWINGS

The above mentioned and other features of this invention will become more apparent and the invention itself will be better understood by reference to the following description of embodiments of the invention taken in conjunction with the accompanying drawings, wherein.

Corresponding reference characters indicate corresponding parts throughout the views of the drawings.

DETAILED DESCRIPTION OF THE INVENTION

Figure 1:
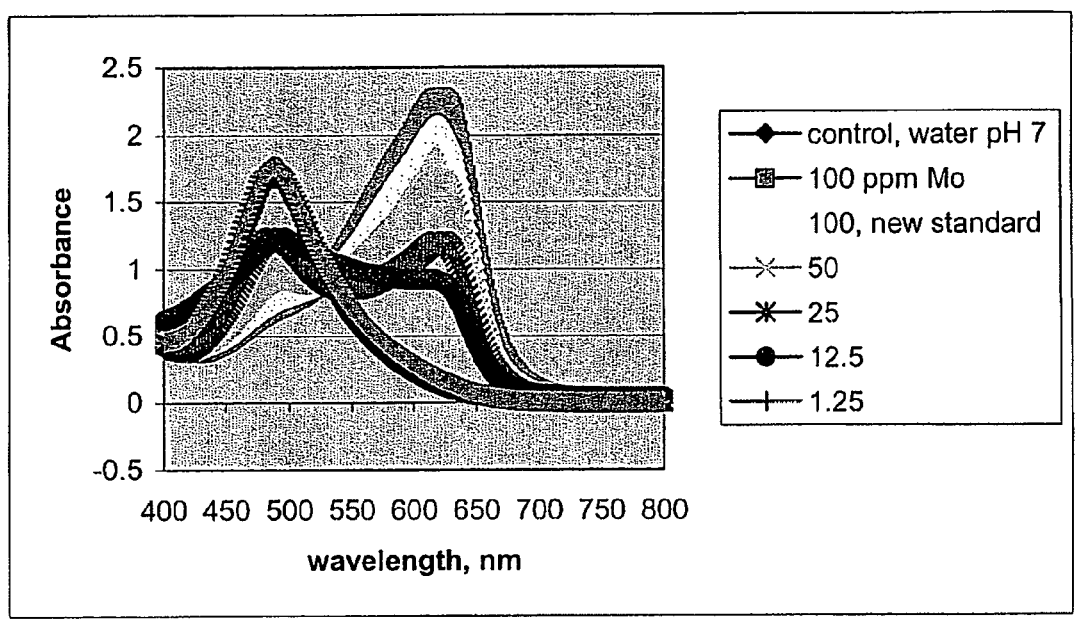
FIG. 1 illustrates absorption spectra of a molybdate sensor film according to one embodiment of the invention at different molybdate concentrations.

The invention will now be described in the following detailed description with reference to the drawings, wherein preferred embodiments are described in detail to enable practice of the invention. Although the invention is described with reference to these specific preferred embodiments, it will be understood that the invention is not limited to these preferred embodiments. But to the contrary, the invention includes numerous alternatives, modifications and equivalents as will become apparent from consideration of the following detailed description.

Disclosed are improved sensor material compositions and methods for determining the concentration of chemical species in a sample at trace concentrations. According to the invention, the sensor materials change their optical property in the ultraviolet (UV), visible, or near-infrared (IR) spectral range upon exposure to trace concentrations of the chemical species. The film is a polymer-based composition generally including a chemically sensitive analyte-specific reagent (for example, a fluorescent or calorimetric indicator), a polymer matrix or combination of polymer matrices, and auxiliary minor additives, wherein the film is produced from a solution of the components in a common solvent or solvent mixture. The analyte-specific reagent is immobilized within the polymer matrix to form the sensor film. Examples of additives are surfactants and internal buffers. Other additives can be also included. The polymers utilized in the sensor film are permeable to selected analytes where an analyte is a certain chemical species or class of chemical species detected by the sensor. The analyte-specific reagent undergoes changes in its optical properties (e.g., absorbance, fluorescence) as a function of analyte concentration. Desirably, the analyte-specific reagent undergoes the changes in its optical property outside the film where the change in response is not affected by the presence of interfering species as provided by the sensor formulation. Measurements are performed using ultraviolet-visible-near-IR detection systems known to those skilled in the art.

The desired response is achieved by tailoring the composition of the sensor film where the composition includes additional components in the film. For example, the desired sensor response is achieved by tailoring the oxidation potential of the immobilized analyte-specific reagent with selection of the polymer matrix components where the polymer matrix components are additional polymers. It is desired that the sensor film be self-contained so it does not have a need for auxiliary reagents outside the film.

The polymer matrix of the sensor film is preferably a plastic film, i.e., a resin film. The resin utilized to form the polymer support depends on the sensor applications. The resin is dissolved in the solvent so that the analyte-specific reagent becomes dispersed in the liquid medium. Alternatively, the analyte-specific reagent may be applied directly to an already formed plastic film. In one embodiment, a polymer film is made and a solvent is removed from the film by any known means such as evaporation, followed by the exposure of the dry film to a cocktail containing at least one reagent. In this way, a reagent is incorporated into the film. In one embodiment, the sensor film is prepared by coating a clear plastic surface with a thin layer of the chemical mixture and allowed to dry over a period of several hours in air the dark. The final film thickness is desirably between about 0.1 and about 200 microns, more preferably 0.5-100 microns and more preferably 1-50 microns.

For evaluation of response, the film is exposed to aqueous samples of analyte. Desirably, the amount of the aqueous sample of the analyte ranges between about 30 µL and about 50 µL of sample, however other amounts are contemplated without departing from the scope of the invention. Exposure time is desirably between about 0.5-1000 seconds, more preferably 1-500 seconds, and more preferably 5-300 seconds. In one embodiment, the water sample is then removed before measurement of the sensor film. Alternately, the water sample can be present during the measurement. In one yet another embodiment, the measurement is done continuously before water exposure, during water exposure, and after water exposure. In a further embodiment, the measurement is done continuously before water exposure and during water exposure.

The film is measured for analyte response using conventional optical scanning equipment. In one embodiment, measurements of optical response can be performed using an optical system that included a white light source (such as a Tungsten lamp available from Ocean Optics, Inc. of Dunedin, Fla.) and a portable spectrometer (such as Model ST2000 available from Ocean Optics, Inc. of Dunedin, Fla.). The spectrometer is equipped with a 600-grooves/mm grating blazed at 400 nm and a linear CCD-array detector. Desirably, the spectrometer covers the spectral range from 250 to 800 nm and to 1100 nm with efficiency greater than 30%. Light from the lamp is focused into one of the arms of a "six-around-one" bifurcated fiber-optic reflection probe (such as Model R400-7-UV/VIS available from Ocean Optics, Inc. of Dunedin, Fla.). The common arm of the probe illuminates the sensor material. The second arm of the probe is coupled to the spectrometer. For fluorescence measurements light from a source is prefiltered to select an excitation wavelength of interest. Fluorescence emission is collected with the same setup but including an emission long-pass filter. Other known methods of measuring the response may also be used.

It is understood that the polymeric material used to produce the sensor film may affect the detection properties such as selectivity, sensitivity, and limit of detection. Thus, suitable materials for the sensor film are selected from polymeric materials capable of providing the desired response time, a desired permeability, desired solubility, degree of transparency and hardness, and other similar characteristics relevant to the material of interest. Suitable polymers which may be used as polymer supports in accordance with the present disclosure are hydrogels. As defined herein, a hydrogel is a three dimensional network of hydrophilic polymers which have been tied together to form water-swellable but water insoluble structures. The term hydrogel is to be applied to hydrophilic polymers in a dry state (xerogel) as well as in a wet state as described in U.S. Pat. No. 5,744,794.

A number of different methods may be used to tie these hydrogels together. First, tying of hydrogels via radiation or free radical cross-linking of hydrophilic polymers may be utilized, examples being poly(hydroxyethylmethacrylates), poly(acrylic acids), poly(methacrylic acids), poly(glyceryl methacrylate), poly(vinyl alcohols), poly(ethylene oxides), poly(acrylamides), poly(N-acrylamides), poly(N,N-dimethylaminopropyl-N'-acrylamide), poly(ethylene imines), sodium/potassium poly(acrylates), polysaccharides, e.g. xanthates, alginates, guar gum, agarose etc., poly(vinyl pyrrolidone) and cellulose based derivatives. Second, tying via chemical cross-linking of hydrophilic polymers and monomers with appropriate polyfunctional monomers may be utilized, examples including poly(hydroxyethylmethacrylate) cross-linked with suitable agents such as N,N'-methylenebisacrylamide, polyethylene glycol diacrylate, triethylene glycol diacrylate, tetraethylene glycol dimethacrylate, tripropylene glycol diacrylate, pentaerythritol tetraacrylate, di-trimethylolpropane tetraacrylate, dipentaerythritol pentaacrylate, trimethylolpropane triacrylate, pentaerythritol triacrylate, propoxylated glyceryl triacrylate, ethoxylated pentaerythritol tetraacrylate, ethoxylated trimethylolpropane triacrylate, hexanediol diacrylate, hexanediol dimethacrylate and other di- and tri-acrylates and methacrylates; the copolymerisation of hydroxyethylmethacrylate monomer with dimethacrylate ester crosslinking agents; poly(ethylene oxide) based polyurethanes prepared through the reaction of hydroxyl-terminated poly(ethylene glycols) with polyisocyanates or by the reaction with diisocyanates in the presence of polyfunctional monomers such as triols; and cellulose derivates cross-linked with dialdehydes, diepoxides and polybasic acids. Third, tying via incorporation of hydrophilic monomers and polymers into block and graft copolymers, examples being block and graft copolymers of poly(ethylene oxide) with suitable polymers such as poly(ethyleneglycol) (PEG), acrylic acid (AA), poly(vinyl pyrrolidone), poly(vinyl acetate), poly(vinyl alcohol), N,N-dimethylaminoethyl methacrylate, poly(acrylamide-co-methyl methacrylate), poly(N-isopropylacrylamide), poly(hydroxypropyl methacrylate-co-N,N-dimethylaminoethyl methacrylate); poly(vinyl pyrrolidone)-co-polystyrene copolymers; poly(vinyl pyrrolidone)-co-vinyl alcohol copolymers; polyurethanes; polyurethaneureas; polyurethaneureas based on poly(ethylene oxide); polyurethaneureas and poly(acrylonitrile)-co-poly(acrylic acid) copolymers; and a variety of derivatives of poly(acrylonitriles), poly(vinyl alcohols) and poly(acrylic acids). Molecular complex formation may also occur between hydrophilic polymers and other polymers, examples being poly(ethylene oxides) hydrogel complexes with poly(acrylic acids) and poly(methacrylic acids). Last, tying via entanglement cross-linking of high molecular weight hydrophilic polymers, examples being hydrogels based on high molecular weight poly(ethylene oxides) admixed with polyfunctional acrylic or vinyl monomers.

As noted above, copolymers or co-polycondensates of monomeric constituents of the above-mentioned polymers, and blends of the foregoing polymers, may also be utilized. Examples of applications of these materials are in Michie, et al., "Distributed pH and water detection using fiber-optic sensors and hydrogels," J. Lightwave Technol. 1995, 13, 1415-1420; Bownass, et al., "Serially multiplexed point sensor for the detection of high humidity in passive optical networks," Opt. Lett. 1997, 22, 346-348; and U.S. Pat. No. 5,744,794.

As set forth above, the hydrogel making up the polymer matrix is dissolved in a suitable solvent including, but not limited to di(ethylene glycol) methyl ether and ethylene glycol phenyl ether, 1-methoxy-2-propanol, ethanol, acetone, chloroform, toluene, xylene, benzene, isopropyl alcohol, 2-ethoxyethanol, 2-butoxyethanol, methylene chloride, tetrahydrofuran, ethylene glycol diacetate, and perfluoro(2-butyl tetrahydrofuran). Generally, the concentration of the solvent in the solution containing the resin is about 70 weight percent or greater, with about 75 weight percent to about 90 weight percent being desirable and about 80 weight percent being preferred. One preferred hydrogel that will be used for exemplary purposes below is poly(2-hydroxyethylmethacrylate) (pHEMA) dissolved in a solvent including of 1-methoxy-2-propanol.

The polymer matrix of the sensor film is preferably permeable to selected analytes. The sensor film may be selectively permeable to analytes on the basis of size (i.e., molecular weight); hydrophobic/hydrophilic properties; phase (i.e., whether the analyte is a liquid, gas or solid); solubility; ion charge; the ability to inhibit diffusion of colloidal or particulate material; or the composition of the water sample besides the analyte itself (for example, pH of the sample during measurements of calcium).

The analyte-specific reagents are incorporated into or applied to the polymer matrix to produce the sensor film. Materials utilized as analyte-specific reagents incorporate dyes and reagents known in the art as indicators. As used herein, "analyte-specific reagents" are indicators that exhibit colorimetric, photorefractive, photochromic, thermochromic, fluorescent, elastic scattering, inelastic scattering, polarization, or any other optical property useful for detecting physical, chemical and biological species. Analyte-specific reagents include organic and inorganic dyes and pigments, nanocrystals, nanoparticles, quantum dots, organic fluorophores, inorganic fluorophores and similar materials.

Examples of compounds which can be used as analyte-specific reagents include organic dyes, organic fluorophores, fluorescent dyes, IR absorbing dyes, UV absorbing dyes, photochromic dyes, thermochromic dyes, sulphonephthalein dyes, and other known dyes that may be used for this purpose. Specific examples of dyes include bromopyrogallol red, xylidyl blue I, chlorophosphonazo III, brilliant green, xanthene dyes such as rhodamine B, rhodamine 6G, eosine, phloxine B and the like, acridine dyes such as acridine orange, acridine red and the like, azo dyes such as ethyl red, methyl red and the like, porphyrin dyes, phthalocyanine dyes, cyanine dyes such as 3,3'-diethylthiacarbocyanine iodide, 3,3'-diethyloxadicarbocyanine iodide and the like, merocyanine dyes, styryl dyes, oxonol dyes, triarylmethane dyes, methylene blue, phenol blue and the like. Other dyes including pH sensitive dyes such as bromothymol blue and bromocresol green may similarly be used. Fluorescent materials which may be used as analyte-specific reagents bond to specific predetermined locations on the sensor film and fluoresce when excited by a specific optical wavelength. Appropriate wavelengths range from about 200 nm to about 1100 nm, more preferably from about 300 nm to about 1000 nm, with a range of from about 350 nm to about 950 nm being most preferred. In other embodiments, non-fluorescing analyte-specific reagents that bond to specific predetermined locations may be used. Such reagents include light absorbing materials such as near infrared (NIR) absorbing materials. Examples of NIR absorbing materials include carbon black and Poly(styrenesulfonate)/poly(2,3-dihydrothieno(3,4-b)-1,4-dioxin). In one embodiment, the analyte-specific reagent is a light absorbing reagent absorbing light at about 620-670 nm. In another embodiment, the analyte-specific reagent is a light absorbing reagent absorbing light at about 750-820 nm. In another embodiment, the analyte-specific reagent is a light absorbing reagent absorbing light at about 380-420 nm. These dyes may be used singly or in combination depending on the desired application. The choice of organic compound and amount utilized for a given application depends on the properties of the organic compound and the purpose for which it will be used. For instance, fluorescent dyes may be added to a resin binder at part-per-million concentrations as is known in the art.

In one embodiment of the invention, the analyte-specific reagent is immobilized in the hydrogel matrix by forming an ion pair between the analyte-specific reagent and a lipophilic counter ion, such as a quaternary ammonium ion. It is known that quaternary ammonium ions may cause a change in the absorption spectra of analyte-specific reagents. However, it was unexpectedly discovered that the addition of quaternary ammonium ions, in concentrations substantially higher than the stoichiometric amount required to ion pair an analyte-specific reagent, produced a very significant improvement in the indicator selectivity and sensitivity. As used herein, concentrations substantially higher than the stoichiometric amount required to ion pair means the quaternary ammonium ions are added in a concentration of between about 5-1000 times greater than stoichiometric amounts relative to the indicator. By means of example and not by way of limitation, it has been determined that a preferred molar ratio of 285:1 (quaternary ammonium ion:indicator) is desirable for a particular molybdate sensor. By comparison, an optimum molar ratio of 18:1 was determined for a sulfite sensor. Without being limited to any particular explanation, it is currently believed that the physical change that occurs when amounts of quaternary ammonium ions greater than the critical micelle concentration are present in the film is the formation of micelles that bind more than a single indicator-analyte complex at its surface. Ligand-metal ratios greater than unity are thus formed in the presence of cationic micelles and can lead to enhancements in expected ultraviolet-visible-near-IR spectroscopy responses of the indicator-analyte.

One example of an ion pair to be used below for exemplary purposes and not by way of limitation is Bromopyrogallol Red (BR) and benzyldimethyltetradecylammonium chloride (Zephiramine) for the BP Red-MoO4 indicator system. The presence of quaternary ammonium salts has been shown to induce a significant bathochromic shift of the BP Red-Mo chelate absorption maximum, as well as intensification of the chelate absorption band. The quaternary ammonium salt used in this film was chosen with respect to structure and mass to achieve a shift in a position of peak absorption ($\lambda_{max}$) to longer wavelengths. Table 1 lists the $\lambda$max produced by selected quaternary ammonium salts on pHEMA film when wetted.

TABLE 1

Effect of Quaternary Ammonium and Phosphonium Salt on $\lambda_{max}$ of pHEMA film when wetted with water

| Quaternary ammonium salt | $\lambda$max (nm) |
|---|---|
| Zephiramine(tetradecyldimethylbenzyl-ammonium chloride) | 620 |
| TBAB (tetrabutylammonium bromide) | 615 |
| TBPB (tetra butylphosophonium bromide) | 613 |

The addition of quaternary ammonium salt in concentrations significantly higher than that required to ion pair produced a very significant improvement in the indicator selectivity and sensitivity. A significant absorbance shift, desirably between about 10 nm and about 30 nm, and more desirably about 20 nm, in $\lambda$max to higher wavelength was observed when the quaternary ammonium salts were added in greater than stoichiometric amounts relative to the dye. This shift enables significant improvement in detection sensitivity when the film is measured at a wavelength near the $\lambda$max. Desirably, the measured wavelength is within about 1-80 nm of $\lambda$max. Without being limited to any specific reason, the effect is believed to be the result of the formation of the BP Red-MoO4 chelate of higher order (e.g., higher ligand: metal ratio) on the interface of cationic micelle.

In another embodiment of the invention, multiple transparent hydrogel films are prepared that contain a chemical composition that changes color after being exposed to the sample solution to obtain a quantitative measurement of the sample solution. In one example of this embodiment, multiple films are prepared to be used to determine the alkalinity of the sample solution, and desirably contain a chemical composition that changes color after being exposed to alkaline species in the sample solution. Desirably, between about 2 and 12 transparent films, and more preferably between 2 and 8 transparent films are prepared and are exposed to the sample solution.

The chemical composition added in the hydrogel films comprises a pH indicator, a surfactant, and an acid. Suitable surfactants include quaternary ammonium salt such as cetyltrimethylammonium bromide, tridodecylmethylammonium chloride, tetrabutylammonium bromide, and many others. Desirably, the surfactant reduces or substantially eliminates the amount of indicator leaching in the film. Without the surfactant, indicator leaching will introduce undesirable errors in absorbance measurement. Suitable pH indicator dyes include bromocresol green and bromophenol blue. It is desirable that the pH indicator dye have a pKa value near 4.3.

According to the method disclosed in this embodiment, the multiple hydrogel films in this embodiment each contain a different amount of acid. Some suitable acids are carboxylic acids and aryl- and alkylsulfonic acids such as p-toluenesulfonic acid, however any acid that can be dissolved in the hydrogel media may be used. The acid concentration in each film is different and varies from film to film by a predetermined pattern. The acid concentrations desirably vary between about 0.2 and 50 weight % relative to dry pHEMA (hydrogel). Preferably, the film having the lowest concentration has a concentration between about 0.2 and 20 weight %, and more desirably between about 0.8 and 10 weight %. Preferably, the film having the highest concentration has a concentration between about 20 and 50 weight %, and more desirably between about 25 and 35 weight %. The number of films that are needed to cover a given alkalinity range if a weak acid such as a carboxylic acid is used is fewer than that if a strong acid is used. This is because the weak acid exhibits a flatter titration curve than the strong acid. However, weak acids usually form complexes with ions such as calcium ions that commonly exist in water samples.

When a given amount of sample solution is deposited on the hydrogel films, alkaline species in the sample neutralize the acid added. Since an acid concentration gradient is created by addition of different amount of acid in the film series, a profile of color change is resulted in when the film series (multiple films) is (are) exposed to the sample solution, corresponding to different degree of neutralization. Average absorbance of all the films in the series is used for quantitative determination of sample alkalinity.

The films may be prepared by depositing the polymer solution into wells on a glass slide or other suitable method known to those skilled in the art. In one example, the wells may be created with a die-cut, adhesive-backed polymer mask layer. The films are then exposed to a fixed amount of the sample solution. After the films are exposed, the absorbance of each film is measured using known methods at a wavelength near or at the maximum absorbance peak of the indicator. The average absorbance measured from the sensor films is used to quantify the alkalinity of the sample. This method is based on absorbance measurement and it will still work even if all of films change color. Further, in addition to colorimetric measurements, fluorescence and other optical measurements are possible.

In another embodiment of the invention, we unexpectedly discovered that an addition of a certain polymer as an additive (or blend) to a polymer formulation, provides an enhancement of signal if this additive is at a certain concentration. Above and below this concentration, the effect is diminished. This effect was discovered in the application of dye 2-[2-[3-[(1,3-Dihydro-3,3-dimethyl-1-propyl-2H-indol-2-ylidene) ethylidene]-2-phenoxy-1-cyclohexen-1-yl]ethenyl]-3,3-dimethyl-1-propylindolium perchlorate known as IR 768 perchlorate. The addition of Nafion® resulted in the improvement of the relative response of the sensor film when sensor signal change is normalized by the remaining absorbance at highest tested concentration. Nafion® is a trade name for sulfonated tetrafluoroethylene copolymer from E.I. du Pont de Nemours and Company (Wilmington, Del.).

The present disclosure will now be described more specifically with reference to the following examples. It is to be noted that the following examples are presented herein for purpose of illustration and description; they are not intended to be exhaustive or to limit the disclosure to the precise form disclosed.

EXAMPLE 1

Molybdate Sensor

To a 10.0 g solution of 20% pHEMA (MW 300,000) in 1-methoxy-2-propanol (Dowanol PM), was added 20 mg Bromopyrogallol Red and 40 mg para-toluenesulfonic acid. After stirring for 1 hour, 200 mg benzyldimethyltetradecylammonium chloride (Zephiramine) was added. After an additional 1 hour of stirring, 40 mg L-ascorbic acid was added and the mixture stirred at room temperature until all solids were dissolved (minimum of 12 hours).

The sensor film was prepared by coating a clear plastic surface with a thin layer of the chemical mixture and allowed to dry over a period of several hours in the dark. The final film thickness was between 10 and 20 microns.

The sensor film was exposed to about 30 µL of aqueous samples of molybdate at various concentrations. Exposure time was in general 120 seconds. The water sample was then removed and the film dried under a constant airflow. The sensor film was then measured for molybdate response.

Figure 2:
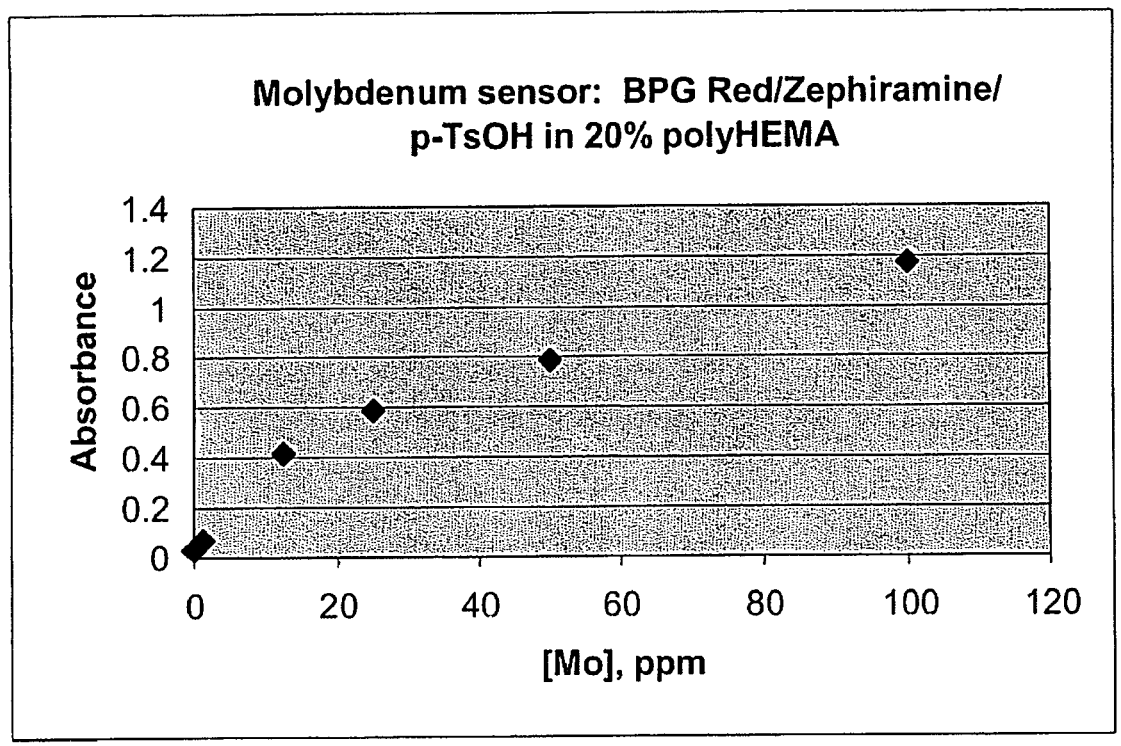
FIG. 2 illustrates a response curve for the sensor film of FIG. 1.
Figure 3:
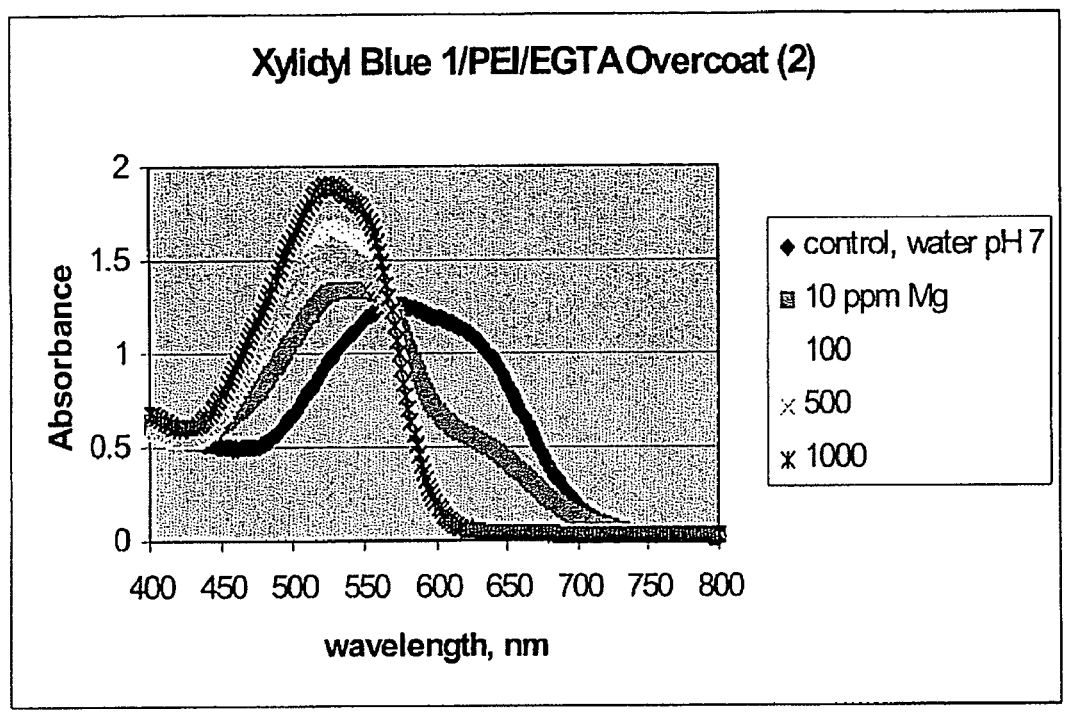
FIG. 3 illustrates absorption spectra of a magnesium sensor according to another embodiment of the invention at different magnesium concentrations.

The sensor film was places in a dark room on a flat surface. The sensor film response was measured using an OceanOptics spectrophotometer equipped with a fiber-optic probe. The probe was oriented at a 90° with respect to the sensor film FIG. 1 shows a typical set of spectra at different molybdate concentrations for the described sensor film. FIGS. 2 and 3 show a typical response curves for the described sensor film.

EXAMPLE 2

Magnesium Sensor

Chemical Mixture Preparation:

To a 10.0 g solution of 20% pHEMA (MW 300,000) in 1-methoxy-2-propanol (Dowanol PM), was added 50 mg Xylidyl Blue 1, sodium salt and 300 mg tetrabutylammonium bromide (TBAB). After stirring for 1 hour, 500 mg of a 40% (w/w) solution of polyethylenimine (low molecular weight Mn approx. 1000, water-free) in 1-methoxy-2-propanol (Dowanol PM) was added. After an addition 1 hour stirring, 400 mg ethylene glycol-bis(aminoethylether)-N,N,N',N'-tetraacetic acid, tetrasodium salt (EGTA-Na4) was added and the mixture stirred at room temperature until all solids were dissolved (minimum of 12 hour).

Figure 4:
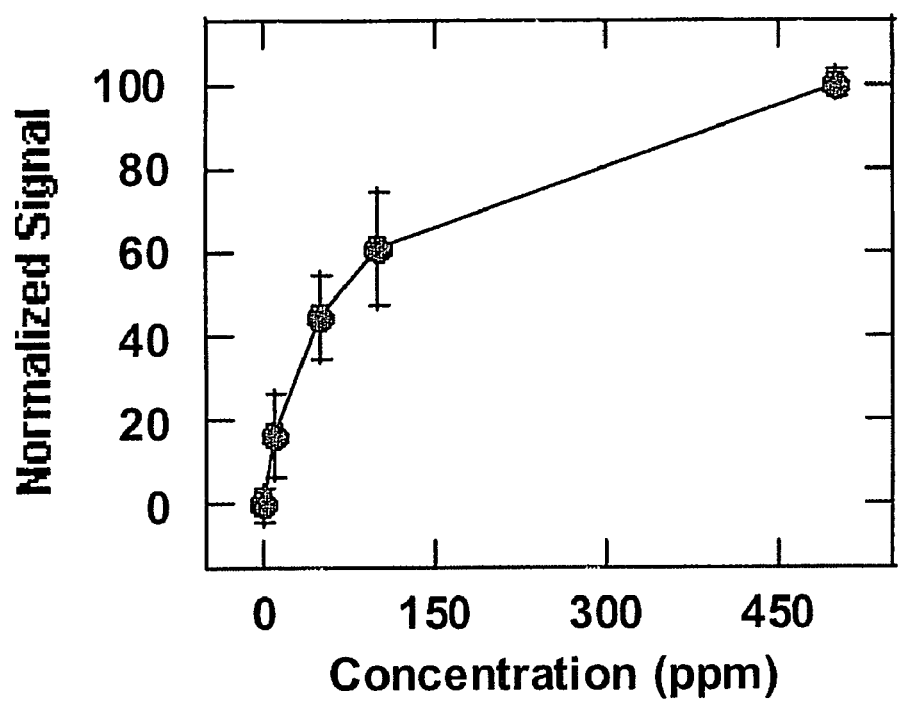
FIG. 4 illustrates a response curve for the sensor film of FIG. 3.

FIG. 3 shows a typical set of spectra at different magnesium concentrations for the described sensor film. FIG. 4 shows a typical response curve for the described sensor film.

EXAMPLE 3

Hardness Sensor

Chemical Mixture Preparation:

To a 10.0 g solution of 20% pHEMA (MW 300,000) in 1-methoxy-2-propanol (Dowanol PM), was added 50 mg Xylidyl Blue I, sodium salt and 500 mg of a 40% (w/w) solution of polyethylenimine (low molecular weight Mn approximately 1000, water-free) in 1-methoxy-2-propanol (Dowanol PM). The mixture was stirred at room temperature until all solids were dissolved (minimum of 12 hour).

Figure 5:
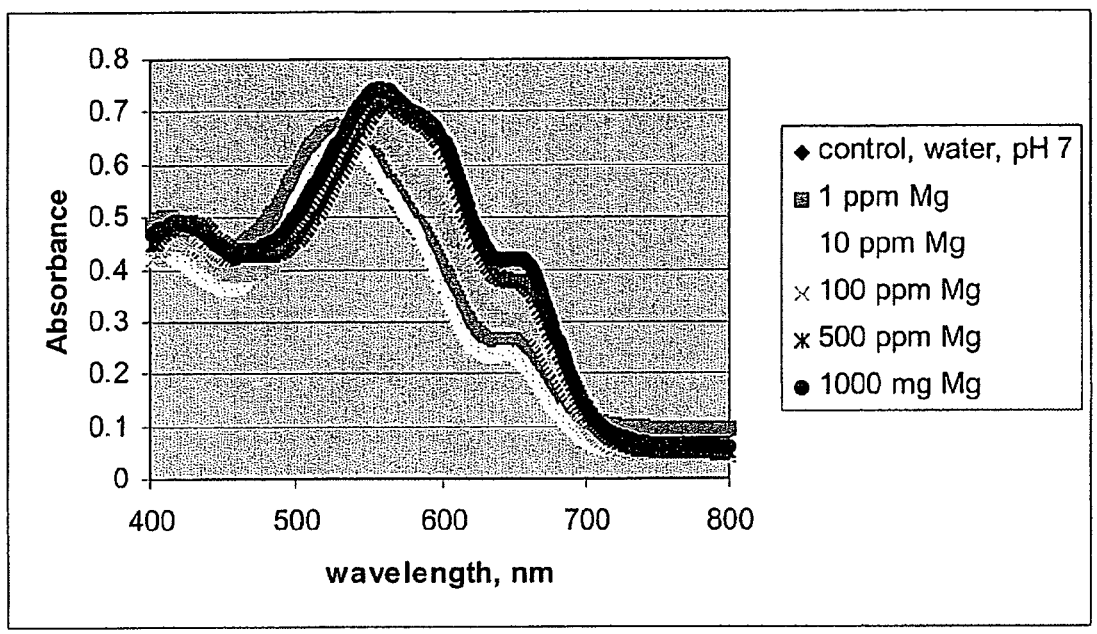
FIG. 5 illustrates absorption spectra of a hardness sensor according to another embodiment of the invention at different concentrations of magnesium.
Figure 6:
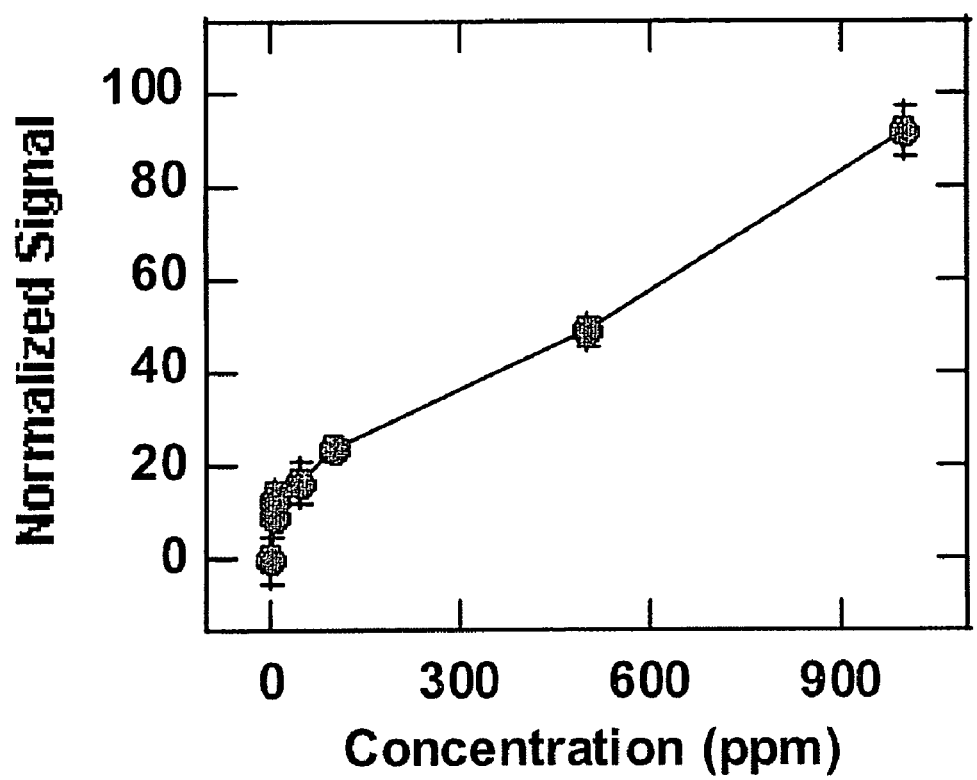
FIG. 6 illustrates a response curve for the sensor film of FIG. 5.

FIG. 5 shows a typical set of spectra at different hardness concentrations for the described sensor film. FIG. 6 shows a typical response curve for the described sensor film.

EXAMPLE 4

Calcium Sensor

Chemical Mixture Preparation:

To a 10.0 g solution of 20% pHEMA (MW 300,000) in 1-methoxy-2-propanol (Dowanol PM), was added 25 mg Chlorophosphonazo III and 200 mg para-toluenesulfonic acid. The mixture was stirred at room temperature for 1 hour, before 60 mg tridocecylmethylammonium chloride (TDMAC) was added. The mixture was stirred at room temperature until all solids were dissolved (minimum of 12 hour).

Figure 7:
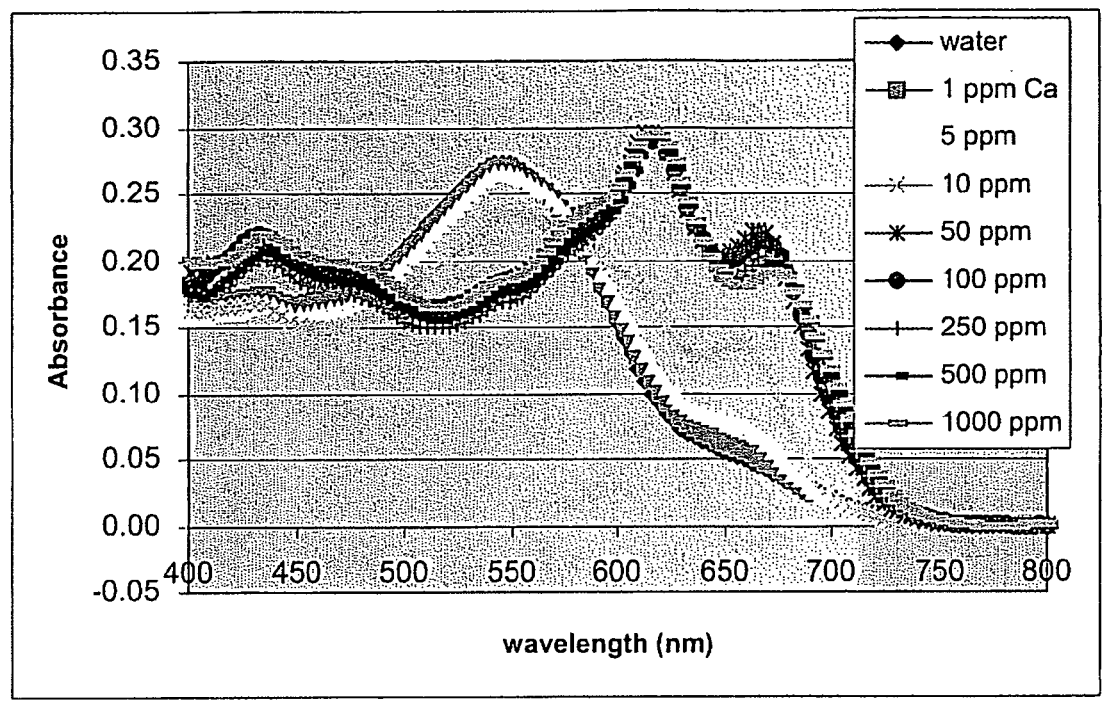
FIG. 7 illustrates absorption spectra of a calcium sensor according to another embodiment of the invention at different calcium concentrations.
Figure 8:
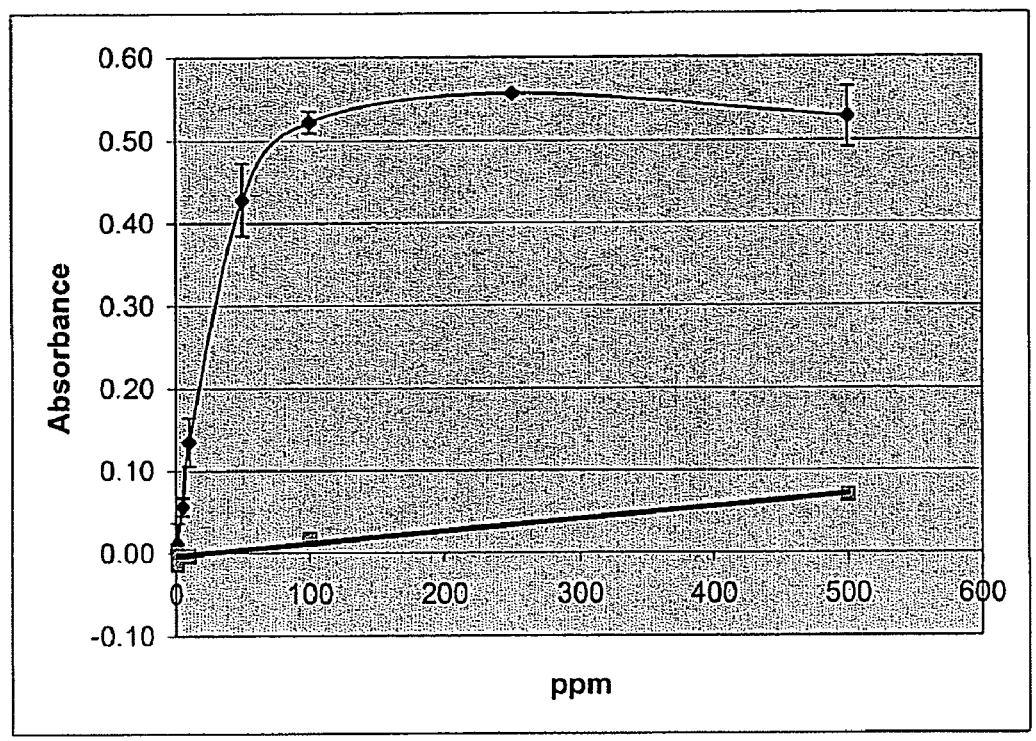
FIG. 8 illustrates a response curves for the sensor film of FIG. 7.

FIG. 7 shows a typical set of spectra at different calcium concentrations for the described sensor film. FIG. 8 shows a typical response curve for the described sensor film.

EXAMPLE 5

Sulfite Sensor

Chemical Mixture Preparation:

To a 10.0 g solution of 20% pHEMA (MW 300,000) in 1-methoxy-2-propanol (Dowanol PM), was added 8 mg Brilliant Green and 120 mg tetrabutylammonium bromide (TBAB). The mixture was stirred at room temperature until all solids were dissolved (minimum of 12 hour).

Figure 9:
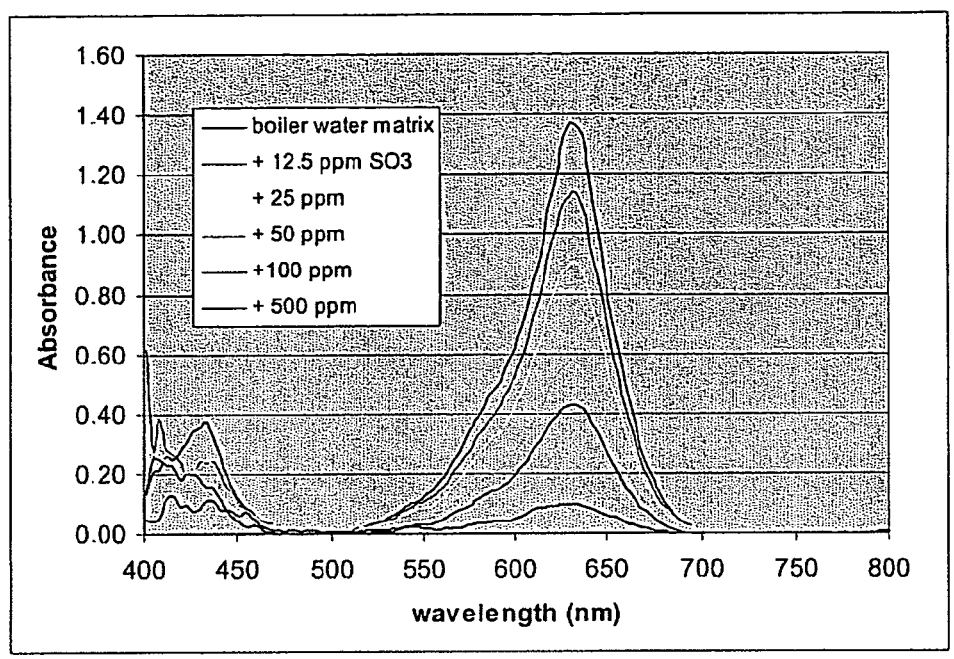
FIG. 9 illustrates absorption spectra of a sulfite sensor according to another embodiment of the invention at different sulfite concentrations.
Figure 10:
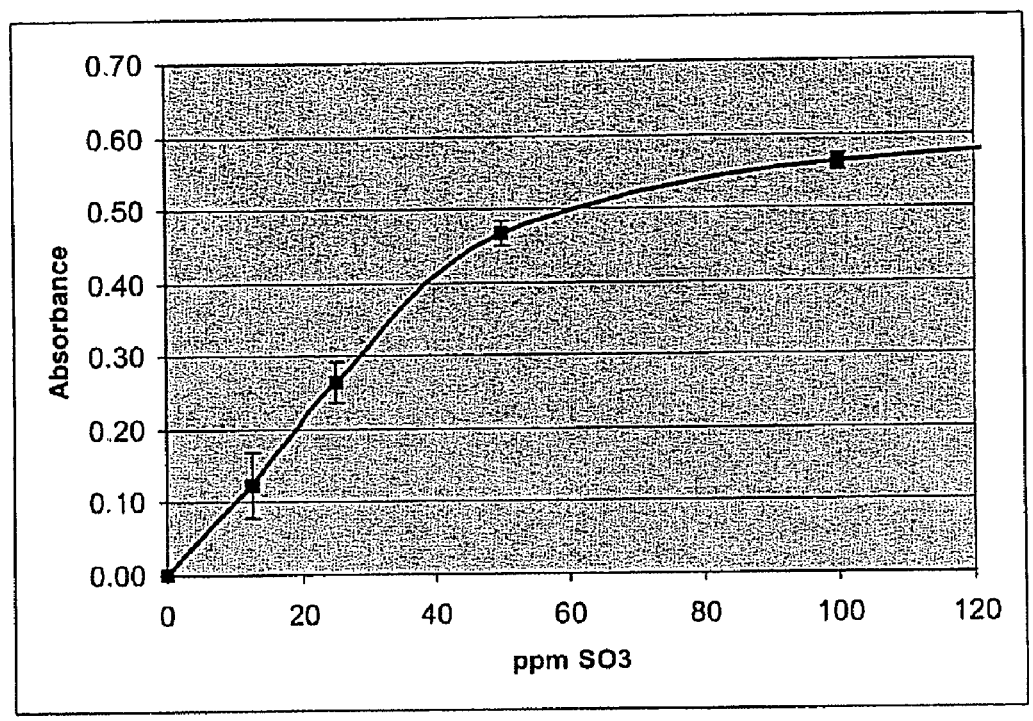
FIG. 10 illustrates a response curve for the sensor film of FIG. 9.

FIG. 9 shows a typical set of spectra at different sulfite concentrations for the described sensor film. FIG. 10 shows a typical response curve for the described sensor film.

EXAMPLE 6

Sulfite Sensor II (Prepared to Withstand Highly Alkaline, High pH Water Samples)

The following example serves to illustrate how it is possible to buffer a chemical film (sulfite) by overcoating a first film with a second buffering film. The two-layer film provides a method to allow measurement of a desired analyte (sulfite) in an extreme water environment (very high pH (pH 12) and very high alkalinity (1000 mg/L M-alkalinity)). Without the overcoating of the first film with the second buffering film, the sensor film tends to respond to the high pH of the water sample and not to the desired analyte (sulfite).

Chemical Mixture I Preparation:

To a 10.0 g solution of 25% pHEMA (MW 300,000) in a 65/35 wt % mixture of di(ethylene glycol) methyl ether (Dowanol DM) and 1-methoxy-2-propanol (Dowanol PM), was added 8 mg Brilliant Green, 120 mg tetrabutylammonium bromide (TBAB), and 36 mg potassium phosphate, monobasic ($KH_2PO_4$) dissolved in 200 mL water. The mixture was stirred at room temperature until all solids were dissolved (minimum of 12 hour). The sensor film was prepared by coating a clear plastic surface with a thin layer of the chemical mixture and allowed to dry over a period of several hours in the dark. The final film thickness was between 5 and 20 microns.

Chemical Mixture II Preparation:

To a 10.0 g solution of 25% pHEMA (MW 300,000) in a 65/35 wt % mixture of di(ethylene glycol) methyl ether (Dowanol DM) and 1-methoxy-2-propanol (Dowanol PM), was added 120 mg tetrabutylammonium bromide (TBAB), and 36 mg potassium phosphate, monobasic ($KH_2PO_4$) dissolved in 200 mL water. The mixture was stirred at room temperature until all solids were dissolved (minimum of 12 hour). Chemical mixture II was coated over the dry chemical mixture I film prepared on a clear plastic surface and was allowed to dry over a period of several hours in the dark. The combined final film thickness between 10 and 40 microns.

Figure 11:
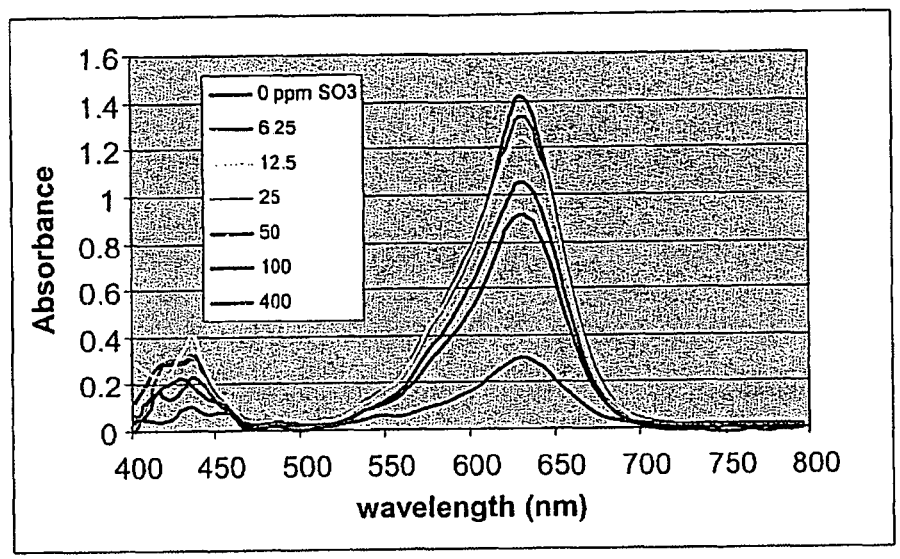
FIG. 11 illustrates a typical set of spectra of a sulfite sensor according to another embodiment of the invention at different sulfite concentrations.
Figure 12:
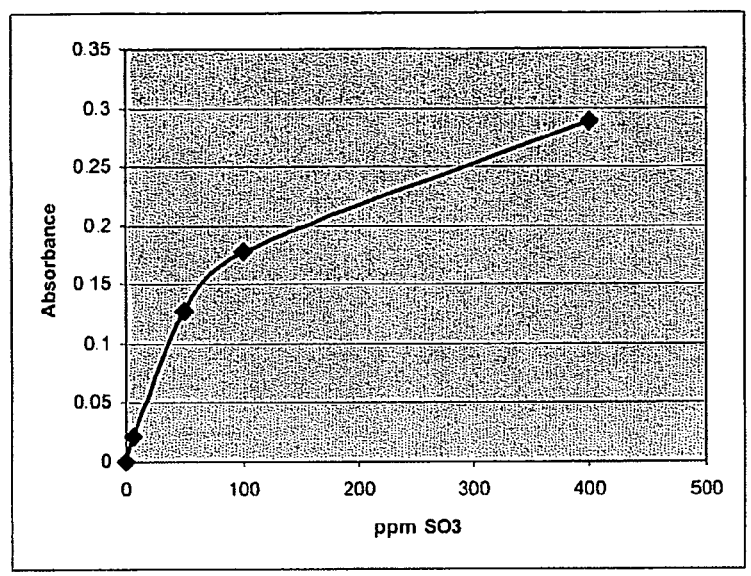
FIG. 12 shows a typical response curve for the sensor film of FIG. 11.

FIG. 11 shows a typical set of spectra at different sulfite concentrations for the described device. Sulfite concentrations were prepared in a highly alkaline (1000 mg/L M-alkalinity) and high pH (ph 12) water matrix. FIG. 12 shows a typical response curve for the described device.

EXAMPLE 7

Alkalinity Sensor

Figure 13:
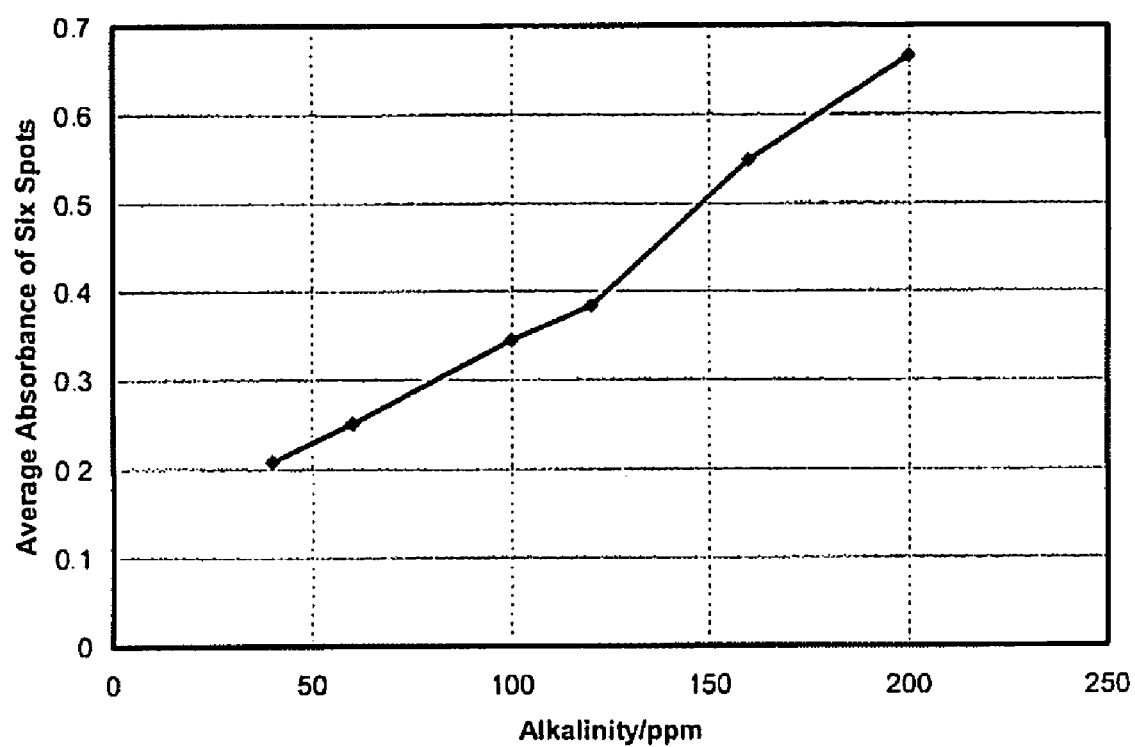
FIG. 13 illustrates a calibration curve for an alkalinity sensor.

The acid used in this example is p-toluenesulfonic acid, and the indicator used is bromoscresol green (pKa=4.9 in aqueous phase). Polymer solution compositions are listed in Table 2. Films were prepared by depositing an 8 μl polymer solution into wells on a glass slide. The wells (5.4 mm diameter and 0.32 mm deep) were created with a die-cut, adhesive-backed polymer mask layer. The mask layer was not removed during the test. Average absorbance at 650 nm is used to quantify the sample total alkalinity. A calibration curve is shown in FIG. 13.

TABLE 2

| Polymer solution composition | | |
|---|---|---|
| Spot # | TsOH (%) | |
| 1 | 0.08 | PHEMA = 10% |
| 2 | 0.16 | BCG = 0.1% |
| 3 | 0.32 | CTAMB = 0.2% |
| 4 | 0.40 | |
| 5 | 0.48 | |
| 6 | 0.64 | |

EXAMPLE 8

Chlorine Sensor

In one embodiment, Nafion® was added to the sensor formulation. Nafion® is a trade name for sulfonated tetrafluoroethylene copolymer from E.I. du Pont de Nemours and Company (Wilmington, Del.). The addition of Nafion® in the improvement of the relative response of the sensor film when sensor signal change is normalized by the remaining absorbance at highest tested concentration. Above and below this concentration, the effect was diminished. One suitable indicator is 2-[2-[3-[(1,3-Dihydro-3,3-dimethyl-1-propyl-2H-indol-2-ylidene)ethylidene]-2-phenoxy-1-cyclohexen-1-yl]ethenyl]-3,3-dimethyl-1-propylindolium perchlorate known as IR 768 perchlorate.

Figure 14:
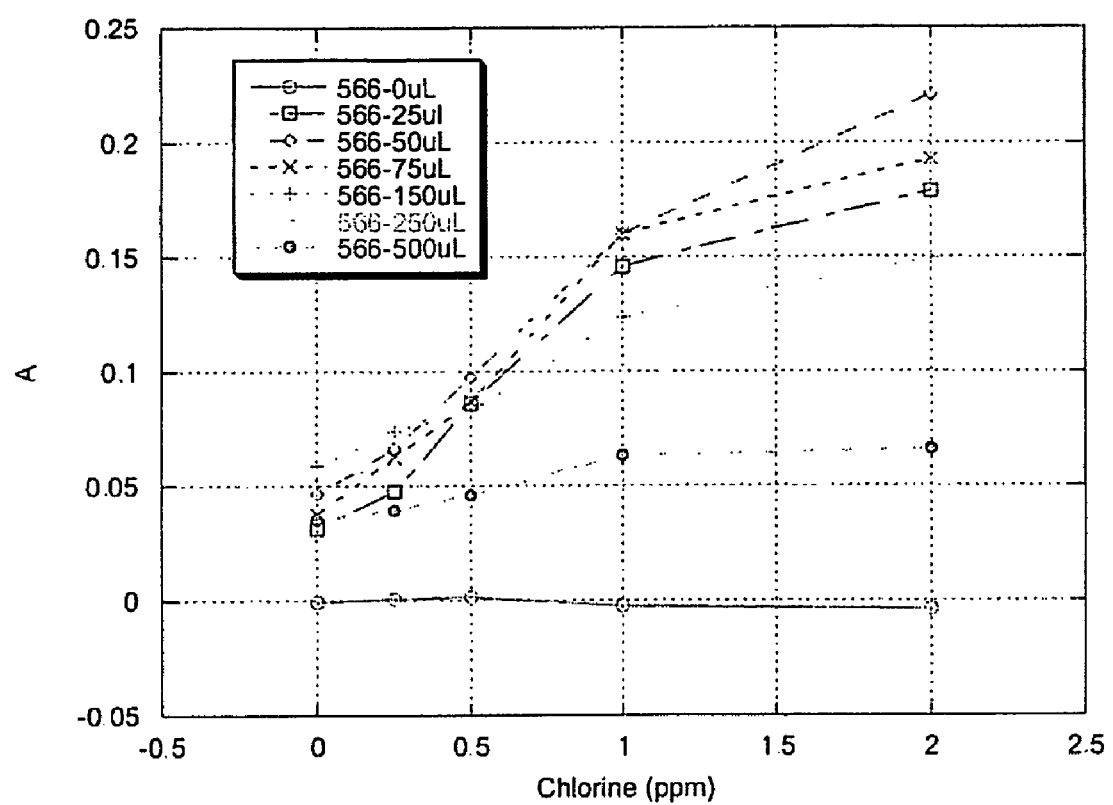
FIG. 14 illustrates the improvement of sensitivity of response upon addition of increasing concentration of Nafion polymer in the pHEMA sensor film.
Figure 15:
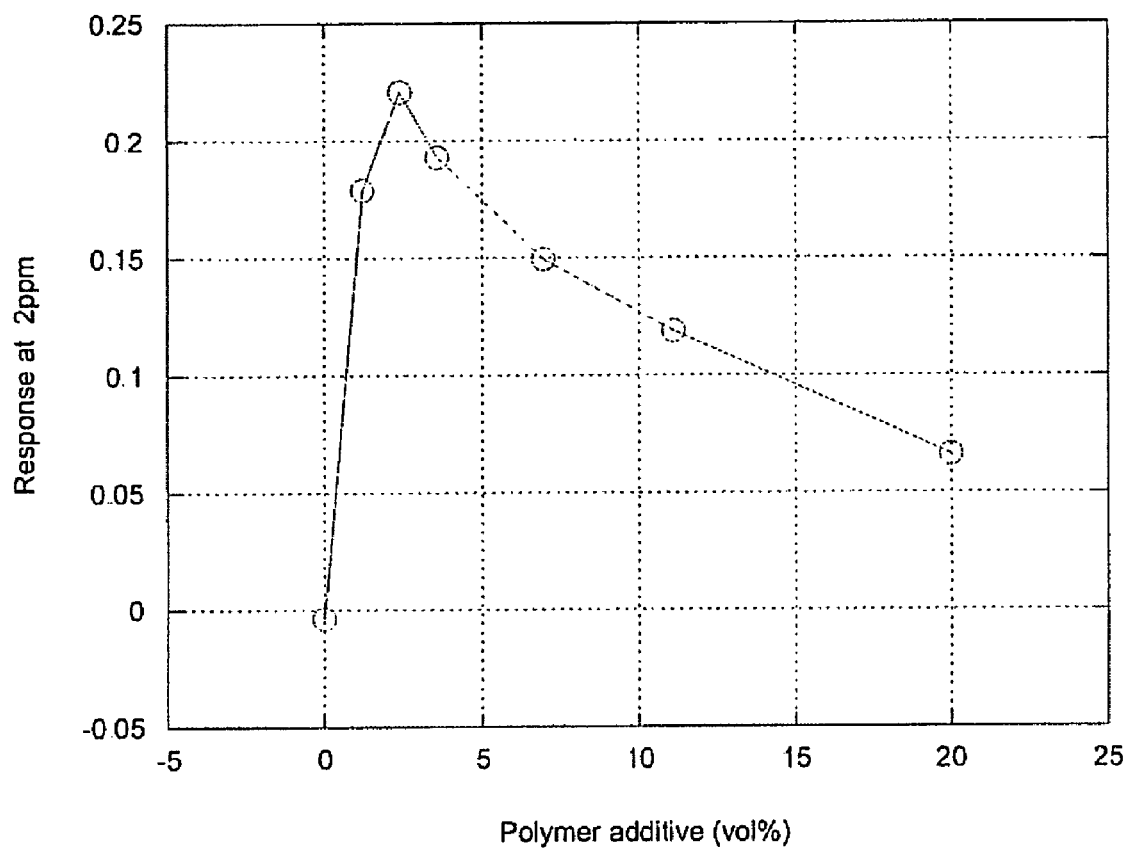
FIG. 15 illustrates the improvement of FIG. 14 plotted as the sensor signal upon exposure to 2 ppm of chlorine demonstrating an existence of a critical non-intuitive region of concentration of Nafion in PHEMA where a maximum sensor response is obtained.

FIG. 14 shows an improvement of sensitivity of response when measured at 566 nm upon addition of increasing amounts of Nafion solution to 2000 μL of dye formulation. This improvement can be plotted as the sensor signal upon exposure to 2 ppm of chlorine as shown in FIG. 15. This figure demonstrates an existence of a critical non-intuitive region of concentration of Nafion in PHEMA where a maximum sensor response is obtained.

While the disclosure has been illustrated and described in typical embodiments, it is not intended to be limited to the details shown, since various modifications and substitutions can be made without departing in any way from the spirit of the present disclosure. As such, further modifications and equivalents of the disclosure herein disclosed may occur to persons skilled in the art using no more than routine experimentation, and all such modifications and equivalents are believed to be within the scope of the disclosure as defined by the following claims.

What is claimed is:

1. A method of quantitatively measuring the concentration of chlorine in a sample solution with a sensor film, said method comprising:
    preparing a hydrogel sensor film having a chemical composition comprising an indicator that changes its optical properties upon being exposed to the chemical species in the sample solution;
    adding a polymer super acid additive during the formation of the hydrogel sensor film such that the polymer super acid additive mixes with the indicator and hydrogel of the sensor film;

immobilizing the indicator in the hydrogel film by forming an ion pair between the indicator and a quaternary ammonium, quaternary phosphonium, quaternary imidazolium, quaternary pyridium, quaternary pyrrolidinium, or quaternary sulfonium ion, wherein the concentration of quaternary ammonium, quaternary phosphonium, quaternary imidazolium, quaternary pyridium, quaternary pyrrolidinium, or quaternary sulfonium salt is 5-1000 times greater than the stoichiometric amount required to ion pair the indicator;

exposing the film to a fixed amount of the sample solution;

measuring the absorbance of the film at a wavelength near the maximum absorbance peak ($\lambda$max) of the indicator using optical scanning equipment; and quantifying the concentration of the chemical species in the sample solution using the average absorbance measured from the sensor film.

2. The method according to claim 1 wherein the sensor film is self-contained such that it does not need auxiliary reagents outside the film to measure the concentration of the chemical species and wherein optical response is in the UV, visible, or near-IR spectral ranges.

3. The method according to claim 1 wherein chemical composition added in the hydrogel films comprises an organic salt or surfactant and an acid.

4. The method according to claim 1 wherein the indicator is pH modified in the hydrogel film by using an acid selected from the group consisting of sulfonic acid, phosphonic acid, carboxylic acid and phenol, wherein the concentration of the acid is substantially higher that the stoichiometric amount required to ion pair the indicator.

5. The method according to claim 1 wherein sensor film is prepared by coating a clear plastic surface with a thin layer of the chemical mixture and allowed to dry, said film having a thickness between 10 and 20 microns.

6. The method according to claim 1 wherein the sensor film is prepared by adding sulfonated tetrafluoroethylene copolymer to pHEMA.

7. The method according to claim 6 wherein the concentration of sulfonated tetrafluoroethylene copolymer is between 1 and 7 percent (volume).

8. The method according to claim 6 wherein the concentration of sulfonated tetrafluoroethylene copolymer is between 0.1 and 7 percent (volume).

9. The method according to claim 1 wherein the sensor film is a two-layer sensor film prepared by overcoating a film containing the indicator, a quaternary ammonium, quaternary phosphonium, quaternary pyridinium, quaternary pyrrolidinium, quaternary imidazolium, or sulfonium salt, and a metal phosphate salt in pHEMA with a second film containing quaternary ammonium, quaternary phosphonium, quaternary pyridinium, quaternary pyrrolidinium, quaternary imidazolium, or sulfonium salt, and metal phosphate salt in pHEMA.

10. The method according to claim 1 wherein said polymer additive is sulfonated tetrafluoroethylene copolymer.

11. The method according to claim 1 wherein the polymer additive is sulfonated tetrafluoroethylene copolymer and the indicator is 2-[2-[3-[(1,3-Dihydro-3,3-dimethyl-1-propyl-2H-indol-2-ylidene)ethylidene]-2-phenoxy-1-cyclohexen-1-yl]ethenyl]-3,3-dimethyl-1-propylindolium perchlorate.

12. The method according to claim 1 wherein the sample solution is present when the absorbance is measured.

13. The method according to claim 1 wherein the absorbance is measured continuously before exposing the sensor film to the sample solution and during exposure of the film to the sample solution.

14. The method according to claim 13 wherein the absorbance is measured continuously before exposing the sensor film to the sample solution, during exposure of the film to the sample solution, and after exposure of the film to the sample solution.

15. The method according to claim 1 wherein analyte-specific reagent (indicator) includes organic and inorganic dyes and pigments, nanocrystals, nanoparticles, quantum dots, organic fluorophores, and inorganic fluorophores.

16. A method of quantitatively measuring the concentration of chlorine in a sample solution with a sensor film, said method comprising:

preparing a pHEMA hydrogel sensor film having a chemical composition comprising an indicator that changes its optical properties upon being exposed to the chemical species in the sample solution;

adding a sulfonated tetrafluoroethylene copolymer additive during the formation of the hydrogel sensor film such that the additive mixes with the indicator and hydrogel of the sensor film, wherein the concentration of sulfonated tetrafluoroethylene copolymer is between 1 and 7 percent (volume);

immobilizing the indicator in the hydrogel film by forming an ion pair between the indicator and a quaternary ammonium, quaternary phosphonium, quaternary imidazolium, quaternary pyridium, quaternary pyrrolidinium, or quaternary sulfonium ion, wherein the concentration of quaternary ammonium, quaternary phosphonium, quaternary imidazolium, quaternary pyridium, quaternary pyrrolidinium, or quaternary sulfonium salt is 5-1000 times greater than the stoichiometric amount required to ion pair the indicator;

exposing the film to a fixed amount of the sample solution;

measuring the absorbance of the film at a wavelength near the maximum absorbance peak ($\lambda$max) of the indicator using optical scanning equipment; and quantifying the concentration of the chemical species in the sample solution using the average absorbance measured from the sensor film.

17. The method according to claim 16 wherein the concentration of sulfonated tetrafluoroethylene copolymer is between 0.1 and 7 percent (volume).

* * * * *